US006426438B1

(12) United States Patent
Fischer et al.

(10) Patent No.: US 6,426,438 B1
(45) Date of Patent: Jul. 30, 2002

(54) METHOD FOR PRODUCING 1,6-HEXANEDIOL AND 6-HYDROXYCAPROIC ACID OR THEIR ESTERS

(75) Inventors: Rolf Hartmuth Fischer, Heidelberg; Rolf Pinkos; Frank Stein, both of Bad Dürkheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/529,808

(22) PCT Filed: Oct. 16, 1998

(86) PCT No.: PCT/EP98/06574

§ 371 (c)(1),
(2), (4) Date: Apr. 20, 2000

(87) PCT Pub. No.: WO99/25672

PCT Pub. Date: May 27, 1999

(30) Foreign Application Priority Data

Nov. 14, 1997 (DE) .......................................... 197 50 532

(51) Int. Cl.$^7$ ................................................ C07C 27/00
(52) U.S. Cl. ........................................ 568/864; 568/861
(58) Field of Search .................................. 568/853, 852, 568/861, 866, 867, 854, 864; 562/579; 560/179

(56) References Cited

U.S. PATENT DOCUMENTS 5,406,004 A * 4/1995 Eastland et al. ............. 568/831
5,696,303 A * 12/1997 Darsow et al. ............. 568/864

FOREIGN PATENT DOCUMENTS

EP    721 928 A2 * 7/1996

* cited by examiner

Primary Examiner—Samuel Barts
Assistant Examiner—Elvis O. Price
(74) Attorney, Agent, or Firm—Keil & Weinkauf

(57) ABSTRACT

A process for the preparation of 1,6-hexanediol and 6-hydroxycaproic acid or esters thereof by catalytic hydrogenation of adipic acid, adipic acid monoesters or adipic acid diesters or streams of starting material which contain adipic acid or esters thereof as essential constituents, in which the bottom product obtained in the distillation of the hydrogenation product, following removal of the hexanediol and hydroxycaproic acid or esters thereof, and essentially comprises oligomeric esters of 6-hydroxycaproic acid, is recycled to the hydrogenation, and the resulting mixture of starting material and recycle stream is reacted at from 100 to 300° C., at from 10 to 300 bar in the liquid phase and at a molar ratio of carboxyl groups to be hydrogenated to hydrogen in the reactor of from 1:5 to 1:100 on hydrogenation catalysts is described.

11 Claims, No Drawings

METHOD FOR PRODUCING 1,6-HEXANEDIOL AND 6-HYDROXYCAPROIC ACID OR THEIR ESTERS

The invention relates to a process for the improved preparation of 1,6-hexanediol and 6-hydroxycaproic acid and esters thereof starting from adipic acid or mono- and diesters thereof or hydrocarbon streams which comprise adipic acid or mono- and diesters thereof and 6-hydroxycaproic acid or esters thereof, by catalytic hydrogenation of the acids and/or of the esters and recycling of the dimeric and oligomeric compounds which are formed as the bottom product following distillation of the hydrogenation product.

U.S. Pat. No. 2,066,533 discloses the catalytic partial hydrogenation of dicarboxylic acids and esters thereof to the corresponding hydroxycarboxylic acids or lactones thereof, without producing significant amounts of diols.

EP 724 908 A1 discloses the hydrogenation, on (modified) Raney noble metal catalysts, of adipic acid or esters thereof to 1,6-hexanediol and 6-hydroxycaproic acid or esters thereof.

JP 49 132 003 discloses the hydrogenation of adipic acid on $Mo/Co/SiO_2$ catalysts to give 1,6-hexanediol and 6-hydroxycaproic acid.

The abovementioned processes have the disadvantage that the product mixtures which are produced during the hydrogenation, ie. alcohols and carboxylic acids, contain dimeric and oligomeric esters.

Esters of adipic acid with hexanediol and hydroxycarboxylic acid and esters of hydroxycaproic acid and hexanediol may be mentioned by way of example (these esters are referred to below as dimers). These esters are unavailable for further use to produce 6-hydroxycaproic acid (6-hydroxycaproate) and 1,6-hexanediol, and have, following removal of the desired products by distillation, to be removed in a further process step, such as eg. hydrolysis with water, which is an equilibrium reaction and does not produce complete conversion. The abovementioned processes are thus only economical to a limited extent.

It is an object of the invention to overcome this prior art disadvantage.

Surprisingly, we have found that it is possible to significantly increase the overall yield of 6-hydroxycaproic acid or esters thereof and 1,6-hexanediol using a process for the preparation of 1,6-hexanediol and 6-hydroxycaproic acid or esters thereof by catalytic hydrogenation of adipic acid, adipic acid monoesters or adipic acid diesters or streams of starting materials which contain adipic acid or esters thereof as essential constituents, if the bottom product which is obtained in the distillation of the hydrogenation product, following removal of the hexanediol and hydroxycaproic acid or esters thereof, and essentially comprises oligomeric esters of 6-hydroxycaproic acid, is recycled to the hydrogenation and the resulting mixture of starting material and recycle stream is reacted at from 100 to 300° C. and at from 10 to 300 bar in the liquid phase and at a molar ratio of carboxyl groups to be hydrogenated to hydrogen in the reactor of from 1:5 to 1:100 on hydrogenation catalysts.

It was surprising that the recycled $C_6$-dimers and $C_6$-oligomers can be reacted under the reaction conditions of the hydrogenation of the monomeric acids and esters thereof, without a direct increase in the level of dimers, oligomers and byproducts, to give 1,6-hexanediol and 6-hydroxycaproic acid and esters thereof, and that the selectivity of the reaction is not impaired. It was also surprising that the useful life of the catalyst is not impaired by the recycling, since it would have been assumed that some dimeric and oligomeric compounds deposit on the catalyst, impairing its activity and selectivity as a result.

The alcohol component of the esters of adipic acid and 6-hydroxycaproic acid is preferably methanol, ethanol, n-propanol, i-propanol, n-butanol, i-butanol and n-pentanol. A particular ester of hydroxycaproic acid is the internal ester caprolactone. The starting material used for the hydrogenation is adipic acid or mono- and/or diesters thereof. This starting material may also contain further $C_6$ compounds, eg. 6-hydroxycaproic acid or esters thereof. It is also possible for further non-$C_6$ compounds which do not impair the novel process, eg. acids such as glutaric acid or succinic acid or esters thereof, to be present. Such mixtures are described, for example, in DE-A 19 607 953. The novel process may use, for example, the stream from stage 4 or the top product stream from stage 12 from Example 1.c. of the above patent.

The hydrogenation is preferably carried out in the liquid phase. The hydrogenation catalysts generally used in the novel process are heterogeneous catalysts, but it is also possible to use homogeneous catalysts which are suitable for hydrogenating carbonyl groups. They can either be arranged as fixed bed catalysts or be employed in mobile form, for example in a fluidized bed reactor. Examples of hydrogenation catalysts for this purpose are described, for example, in Houben-Weyl, Methoden der Organischen Chemie, Volume IV/1c, pages 16 to 26.

Of the hydrogenation catalysts to be used according to the invention, preference is given to those containing one or more elements from groups Ib, VIb, VIIb and VIIIb, and IIIa, IVa and Va, of the Periodic Table of the Elements, in particular copper, chromium, rhenium, cobalt, rhodium, nickel, palladium, iron, platinum, indium, tin and/or antimony. Particular preference is given to catalysts containing copper, cobalt and/or rhenium.

The catalysts employed in the novel process may be, for example, precipitated catalysts. Catalysts of this type can be prepared by precipitating their catalytically active components from solutions of salts thereof, in particular from solutions of their nitrates and/or acetates, for example by adding solutions of alkali metal hydroxide and/or alkaline earth metal hydroxide and/or alkali metal carbonate and/or alkaline earth metal carbonate, eg. sparingly soluble hydroxides, oxide hydrates, basic salts or carbonates, then drying the resulting precipitates and subsequently converting them by calcination at, in general, from 300 to 700° C., in particular from 400 to 600° C., into the corresponding oxides, mixed oxides and/or mixed valency oxides, which are reduced, and converted into the actual catalytically active form, by treatment with hydrogen or hydrogen-containing gases, generally at from 50 to 700° C., in particular from 100 to 400° C., to give the relevant metals and/or oxides of lower oxidation state. This reduction is generally continued until water is no longer formed. To prepare precipitated catalysts containing a carrier material, the catalytically active components can be precipitated in the presence of the relevant carrier material. However, it is also possible advantageously for the catalytically active components to be precipitated simultaneously with the carrier material from the relevant salt solutions. The hydrogenation catalysts preferably employed in the novel process are those containing the hydrogenation-catalyzing metals or metal compounds deposited on a carrier material. Apart from the abovementioned precipitated catalysts, which also comprise a carrier material in addition to the catalytically active components, suitable carrier materials for the novel process are, in general, those in which the components catalyzing the hydrogenation have been applied to a carrier material, for example by impregnation.

The way in which the catalytically active metals are applied to the carrier is generally not critical and can be brought about in various ways. The catalytically active metals can be applied to these carrier materials for example by impregnation with solutions or suspensions of the salts or oxides of the relevant elements, drying and subsequent reduction of the metal compounds to the corresponding metals or compounds of a lower oxidation state by means of a reducing agent, preferably using hydrogen or complex hydrides. Another potential way of applying the catalytically active metals to these carriers consists in impregnating the carriers with solutions of salts which readily undergo thermal decomposition, eg. with nitrates, or complex compounds which readily undergo thermal decomposition, eg. carbonyl or hydrido complexes of the catalytically active metals, and heating the carrier impregnated in this way to from 300 to 600° C. for thermal decomposition of the adsorbed metal compounds. This thermal decomposition is preferably carried out under a protective gas atmosphere. Examples of suitable protective gases are nitrogen, carbon dioxide, hydrogen or the inert gases. The catalytically active metals can furthermore be deposited on the catalyst carrier by vapor deposition or by flame spraying. The content of catalytically active metals in these supported catalysts is not in principle critical for success of the novel process. It is self-evident to the person skilled in the art that higher contents of catalytically active metals in these supported catalysts may result in higher space-time conversions than lower contents. The supported catalysts generally used comprise from 0.1 to 90% by weight, preferably from 0.5 to 40% by weight, of catalytically active metals, based on the entire catalyst. Since these contents refer to the entire catalyst including carrier material, but different carrier materials have very different specific gravities and specific surface areas, lower or higher contents than these are also possible without this necessarily having a disadvantageous effect on the result of the novel process. It is, of course, also possible to apply a plurality of catalytically active metals to the particular carrier material. Furthermore, the catalytically active metals can be applied to the carrier for example by the process of DE-A 2 519 817, EP-A 147 219 and EP-A 285 420. The catalytically active metals are present in the catalysts disclosed in the abovementioned publications as alloys which are produced by thermal treatment and/or reduction after, for example, impregnation with a salt or complex of the abovementioned metals.

Activation both of the precipitated catalysts and of the supported catalysts can also take place in situ at the start of the reaction by the hydrogen which is present, but these catalysts are preferably activated separately before being used.

Suitable carrier materials are generally the oxides of aluminum and titanium, zirconium dioxide, silicon dioxide, clays, such as montmorillonites, silicates, such as magnesium or aluminum silicates, zeolites, such as ZSM-5 or ZSM-10 zeolites, or activated carbon. Preferred carrier materials are aluminum oxides, titanium dioxides, silicon dioxide, zirconium dioxide and activated carbon. It is, of course, also possible to use mixtures of various carrier materials as carrier for the catalysts which can be used in the novel process. Examples of heterogeneous catalysts which can be employed in the novel process are the following:

cobalt on activated carbon, cobalt on silicon dioxide, cobalt on aluminum oxide, rhenium on activated carbon, rhenium on silicon dioxide, rhenium/tin on activated carbon, rhenium/platinum on activated carbon, copper on activated carbon, copper/silicon dioxide, copper/aluminum oxide, copper chromite, barium copper chromite, copper/aluminum oxide/ manganese oxide, copper/aluminum oxide/zinc oxide, and the catalysts disclosed in DE-A 3 932 332, U.S. Pat. No. 3,449,445, EP-A 44 444, EP-A 147 219, DE-A 3 904 083, DE-A 2 321 101, EP-A 415 202, DE-A 2 366 264, EP 0 552 463 and EP-A 100 406.

Particularly preferred catalysts contain at least one of the metals copper, cobalt or rhenium.

The novel process can advantageously be carried out continuously using, for example, tubular reactors in which the catalyst is advantageously arranged in the form of a fixed bed.

According to the invention, the molar ratio of groups to be hydrogenated, ie. carboxyl group either as acid group or ester group, to hydrogen in the reactor is between 1:5 and 1:100, preferably between 1:7 and 1:70. The requisite reaction pressure is above 10 bar, preferably 100–300 bar, particularly preferably 150–300 bar. The reaction temperatures are in the range 100–300° C., preferably 130–270° C., particularly preferably 160–240° C. Between 0.05 kg and 5 kg, preferably 0.1 and 3 kg, particularly preferably 0.2 and 1.5 kg, of starting material per hour are passed over the hydrogenation catalyst per part by volume of catalyst (=space velocity).

A solvent is not necessary, although one can be used. Suitable solvents include water or the alcohol of esters used, such as methanol, ethanol, etc. Water is used preferentially when the free acid is used as solvent.

The ratio of the desired products to one another can vary within wide ranges. In the case of relatively low conversions, 6-hydroxycaproic acid or esters thereof dominates. Economical and therefore preferred molar ratios of 1,6-hexanediol to hydroxycaproic acid or esters thereof are from 1:5 to 100:1, preferably 1:2 to 100:1, particularly preferably 1:1 to 100:1.

The ratio can be influenced, for example, by choice of temperature, pressure, space velocity or residence time. The lower the temperature, pressure and residence time and the higher the space velocity, the higher the proportion of hydroxycarpoic acid or esters thereof.

The desired products 1,6-hexanediol and 6-hydroxycaproic acid or esters thereof are obtained in a manner known per se, eg. by distillation under reduced pressure, for example at 10–500 mbar, preferably 15–100 mbar and still temperatures of 100–250° C., preferably 120–220° C. This produces the mixture, which can be recycled to the hydrogenation, whose main constituent is, inter alia, more than 50% by weight, preferably more than 60% by weight and, in particular, more than 70% by weight, of oligomeric 6-hydroxycaproate, as the bottom product of the distillation column. Particularly when the still temperature is above 150° C. and the molar proportion of hydroxycaproic acid or esters thereof to hexanediol in the hydrogenation mixture is greater than 1:5, it is sensible to keep the residence time of the mixture in the still of the distillation column, provided the latter is operated continuously, as short as possible, for example less than 2 hours, preferably less than one hour, particularly preferably less than 0.5 hour, in order to avoid high molecular weight esters from forming in the bottom product, which hinder recycling since they have high melting points which can be above 200° C.

The unreacted adipic acid or esters thereof can of course likewise be recycled to the hydrogenation.

The recycled bottom product can be recycled batchwise, but when the process is carried out on an industrial scale, is preferably recycled continuously. The recycled product stream can be mixed into the fresh feed upstream of the reactor, or fed directly into the reactor as a second feed. If the hydrogenation is carried out, for example, using primary and secondary reactors, the recycled stream can be introduced into either or both. Although there is usually no increase in the level of dimers and oligomers and, in some instances, in byproducts, it may be necessary to discharge a small amount of the bottom product from the distillation. For this purpose, a batchwise procedure generally involves recycling all of the distillation bottom product until there is an increase in the level of undesired products and then, at appropriate intervals, discharging part of or an entire batch of bottom product. Carrying out the process continuously involves recycling at least most of the distillation bottom product and continuously discharging, as necessary, a relatively small amount of the bottom product.

1,6-Hexanediol is a desired monomer building block which is mainly used in the polyester and polyurethane sector. 6-Hydroxycaproic acid and esters thereof are intermediates in the preparation of caprolactone from which polycaprolactones are obtained. The novel process is described in more detail with reference to the following Examples, but is not limited thereto. The analytical results given were determined by gas chromatography using an internal standard and are % by weight.

EXAMPLE 1

25 ml of T 4489 Cu catalyst from Sud-Chemie which had been activated beforehand in a hydrogen stream were introduced into a 25 ml tubular reactor. The reactor was brought to 220 bar and 175° C. by means of external oil heating. A fresh gas stream of 100 liters (STP)/h of hydrogen was established. As a result, 22.5 ml/h of dimethyl adipate were continuously hydrogenated on downward flow through the catalyst bed. Under the reaction conditions the molar ratio of ester groups to be hydrogenated to hydrogen in the reactor was 1:25. After a running in time of 12 h, the product contained (calculated on a methanol-free basis) 35% of dimethyl adipate, 10% of methyl 6-hydroxycaproate, 30% of 1,6-hexanediol, 10% of esters of 6-hydroxycaproic acid and 1,6-hexanediol and 14% of esters of adipic acid, 1,6-hexanediol and methanol. The remainder was other mixed esters and oligomers. Dimethyl adipate, methyl 6-hydroxycaproate and 1,6-hexanediol were distilled off from this mixture. The residue which remained was mixed with fresh dimethyl adipate in the ratio 1:5 and hydrogenated again over the same catalyst under the abovementioned conditions. It is found that the resulting hydrogenation product corresponds to the composition which was obtained without admixture of the distillation bottom product. This fact did not change even after 5 recycles.

EXAMPLE 2

Hydrogenation was carried out as described in Example 1 over a catalyst which comprised 1% of Re and 1% of Pt on aluminum oxide (prepared by applying $PtO_2$ and $Re_2O_7$ to $Al_2O_3$ and subsequent reduction in a hydrogen stream). At a hydrogenation temperature of 163° C. the product comprised (calculated on a methanol-free basis) 1% of n-hexanol, 2% of 1,6-hexanediol, 10% of methyl 6-hydroxycaproate and 73% of dimethyl adipate. The remainder largely comprised dimeric and oligomeric mixed esters, predominantly those of 1,6-hexanediol. After n-hexanol, dimethyl adipate, methyl 6-hydroxycaproate and 1,6-hexanediol had been removed by distillation, the distillation bottom product which remained was mixed with fresh dimethyl adipate in the ratio 1:6 and rehydrogenated. The composition of the hydrogenation product remained practically unchanged.

We claim:
1. A process for the preparation of 1,6-hexanediol and 6-hydroxycaproic acid or esters thereof with monoalcohols by catalytic hydrogenation of adipic acid, adipic acid monoesters or adipic acid diesters or streams of starting material which contain adipic acid or esters thereof as essential constituents, which comprises recycling the bottom product which is obtained in the distillation of the hydrogenation product, following removal of the hexanediol and hydroxycaproic acid or esters thereof, and essentially comprises oligomeric esters of 6-hydroxycaporic acid to the hydrogenation, and reacting the resulting mixture of starting material and recycle stream at from 100 to 300° C. and at from 10 to 300 bar in the liquid phase and at a molar ratio of carboxyl groups to be hydrogenated to hydrogen in the reactor of from 1:5 to 1:100 on hydrogenation catalysts.

2. A process as claimed in claim 1, which comprises carrying out the hydrogenation on a fixed bed catalyst.

3. A process as claimed in claim 1, which comprises carrying out the hydrogenation on hydrogenation catalysts which comprise, as hydrogenation-active constituents, one or more elements of groups Ib, VIb, VIIb and VIIIb, and IIIa, IVa and Va, of the Periodic Table of the Elements.

4. A process as claimed in claim 1, which comprises carrying out the hydrogenation on hydrogenation catalysts which comprise, as hydrogenation-active constituents, one or more elements selected from the group consisting of copper, chromium, rhenium, cobalt, rhodium, nickel, palladium, iron, platinum, indium, tin and antimony.

5. A process as claimed in claim 4, which comprises carrying out the hydrogenation using supported catalysts.

6. A process as claimed in claim 1, which comprises using a hydrogenation catalyst containing at least copper, cobalt or rhenium.

7. A batch process as claimed in claim 1, in which all of the distillation bottom product of the hydrogenation product is repeatedly recycled, and only when there is an increase in the level of byproducts is some of the bottom product discharged.

8. A continuous process as claimed in claim 1, in which at least most of the distillation bottom product is continuously recycled and, as necessary, a relatively small amount of the bottom product is continuously discharged.

9. A process as claimed in claim 1, wherein, by adjusting the hydrogen excess, the residence time and, if necessary, other reaction parameters, a molar ratio of 1,6-hexanediol to 6-hydroxycaproic acid or esters thereof in the hydrogenation product between 1:5 to 20:1 is established.

10. A process as claimed in claim 1, wherein, said monoalcohols are selected from the group consisting of menthanol, ethanol, n-propanol, i-propanol, n-butanol, i-butanol and n-pentanol.

11. A process as claimed in claimed 1, wherein said bottom product consists of more than 50% by weight oligomeric 6-hydroxycaproate.

* * * * *